United States Patent [19]

Shimizu et al.

[11] Patent Number: 4,892,625
[45] Date of Patent: Jan. 9, 1990

[54] METHOD FOR PRODUCING HIGH PURITY CHEMICALS

[75] Inventors: Shumpei Shimizu, Moses Lake, Wash.; Mamoru Yoshizako, Machida, Japan; Toshitsura Cho, Kawasaki, both of Japan

[73] Assignees: Tama Chemicals Co., Ltd., Japan; Moses Lake Industries, Inc., Japan

[21] Appl. No.: 65,481

[22] Filed: Jun. 23, 1987

[30] Foreign Application Priority Data

Jan. 27, 1987 [JP] Japan .................... 62-015219

[51] Int. Cl.⁴ .................................... B01D 3/00
[52] U.S. Cl. .................. 203/86; 202/267.1; 203/100; 423/484; 423/488
[58] Field of Search .......... 203/DIG. 2, 86, 100; 202/267.1; 423/488, 484; 55/522; 422/202

[56] References Cited

U.S. PATENT DOCUMENTS

| | | | |
|---|---|---|---|
| 961,530 | 6/1910 | Quayle | 422/202 |
| 993,868 | 5/1911 | Pauling | 203/100 |
| 1,917,272 | 7/1933 | Pobielniak | 203/DIG. 2 |
| 2,167,395 | 7/1939 | Thomas | 203/DIG. 2 |
| 2,387,479 | 10/1945 | Todd | 203/100 |
| 2,530,735 | 11/1950 | Schaumann | 203/86 |
| 2,990,341 | 6/1961 | Graybill | 203/86 |
| 3,091,577 | 5/1963 | Pequignot | 203/86 |
| 3,325,376 | 6/1967 | Eckert | 202/158 |
| 3,431,083 | 3/1969 | Bergstrand | 422/197 |
| 4,202,736 | 5/1980 | Marcovich et al. | 203/86 |

FOREIGN PATENT DOCUMENTS

| | | | |
|---|---|---|---|
| 0075664 | 6/1977 | Japan | 203/DIG. 2 |
| 61-151002 | 7/1986 | Japan . | |
| 61-191502 | 8/1986 | Japan . | |
| 269497 | 10/1950 | Switzerland . | |
| 0345579 | 3/1931 | United Kingdom | 203/86 |

*Primary Examiner*—Virginia Manoharan
*Attorney, Agent, or Firm*—Armstrong, Nikaido, Marmelstein, Kubovcik & Murray

[57] ABSTRACT

A distillable liquid containing non-volatile impurities is freed of those impurities by boiling the liquid to form vapors of the liquid, passing the vapors through a packed column heated to a temperature such that liquid entrained in the vapors is completely vaporized and the non-volatile impurities remain in the packed column, and condensing the vapors from the column.

4 Claims, 2 Drawing Sheets

METHOD FOR PRODUCING HIGH PURITY CHEMICALS

BACKGROUND OF THE INVENTION

Field of the Invention

This invention concerns a method for producing chemicals of high purity. More particularly, it relates to a method and apparatus for producing chemicals of high purity by separating and removing non-volatile impurities contained in trace amounts in chemicals.

Recent developments in semiconductors, optical fibers, fine ceramics, etc., have created a need for higher purity industrial materials, particularly those low in non-volatile impurities such as metal impurities and high molecular weight impurities. Further, recent developments in microanalysis have made it possible to analyze metals to parts per billion or parts per trillion. High purity for the various analytic reagents used in microanalysis is required.

Distillation has usually been employed to purify starting materials and analytic reagents which are liquid and thermally stable. For instance, Japanese Patent Laid-Open Publication No. Sho 61-191502 describes a method of purifying hydrofluoric acid containing arsenic compounds by adding a halogen flouride to the hydrofluoric acid to react with the arsenic compound and then purifying the hydrofluoric acid by distillation.

Purification by distillation includes a procedure for heating a liquid to its boiling point, and cooling the evolved vapors back to the liquid state. For high purification, redistillation can be effected in one distillation step by enlarging the contact section of the vapors and the liquid between the heating portion and the condensing portion. If the leaching of impurities from the distillation device is eliminated and if there is no entrainment in which minute droplets are scattered in the vapors and carried in the gas stream, it would be possible to produce chemicals of super high purity, for example, with regard to metal impurities in the range of parts per billion or parts per trillion.

However, the phenomenon of entrainment in purification by distillation cannot be prevented completely even if a rectification means is employed. If it is intended to reduce the phenomenon of entrainment, the distillation or rectification has to be carried out very slowly, whereby the yield per unit time is decreased. Thus, it is extremely uneconomical from an industrial point of view to purify chemicals to super high purity by distillation or rectification. At present, to attain a proper degree of purity, small amounts of the chemicals in analytical reagents for which super high purity is required are purified in the laboratory each time they are needed.

Object and Summary of the Invention

Accordingly, it is an object of this invention to provide a method and apparatus for producing chemicals of high purity as industrial starting materials and as analytical reagents for microanalysis.

Further, another object of this invention is to provide an apparatus for producing highly pure chemicals used for the production of industrial starting materials and analytical reagents of such high purity.

Specifically, this invention concerns a method of producing chemicals of high purity by distilling the materials to be purified in a distillation device comprising a heating section for heating the materials to be distilled, a contact section including contact members for contacting vapors of the materials being distilled, and a condensing section for condensing the vapors passing through the contact section. To eliminate non-volatile impurities in the condensate, the contact section is heated to a temperature at least higher than the boiling point of the material being distilled.

This invention also provides an apparatus for producing chemicals of high purity, that is, a distillation apparatus comprising a heating section for heating the material to be distilled, a contact section including contact members in contact with the vapors of the material being distilled and a condensing section for condensing the vapors passing through the contact section. A heating means is disposed in the contact section for heating the contact section at least to a temperature high than the boiling point of the material being distilled.

In this invention, the heating section portion of the apparatus for heating the material to be distilled may be the same as that used for heating the material to be distilled in an ordinary distillation apparatus. The same contact section as employed in an ordinary distillation apparatus may be used, and further the same condensing section as usually used in an ordinary distillation apparatus may also be used.

Referring then to the contact members disposed in the contact section, they may be either trays such as perforated plates or bubble plates, or packings of appropriate shape and size such as broken pieces, spheres, raschig rings, saddles, etc. It is, of course, necessary that the contact member be inert to the material being distilled. The contact member can be silica gel, alumina, teflon, glass, molten synthetic quartz, high purity graphite and various kinds of thermally and chemically stable plastics, appropriate for use depending on the kind of material being distilled.

The heating means for heating the contact section can include, for example, external heating means such as by ohmic heat generation members, an IR lamp, hot gas etc., by direct current supply to the contact member disposed in the contact section, and by high frequency heating means such as high frequency induction heating and high frequency dielectric heating.

In this invention, the heating condition in the heating section and the heating conditions in the contact section may be set so that the vapors of the material to be distilled pass through the contact section at a predetermined velocity and are heated at a temperature higher than the boiling point of the materials to be distilled. The heating temperature in the contact section may be such that the material to be distilled can completely be vaporized in the contact section and usually it is desirable to heat the vapors to a temperature higher by about 1°–200° C. and, preferably, by about 1°–100° C. than the boiling point of the material being distilled. Further, the velocity at which the vapors of the material being distilled pass through the contact section (the distillation rate of the material being distilled) is preferably from 0.01 to 10 sec$^{-1}$ and, more preferably, from 0.05 to 5 sec$^{-1}$ as expressed by the flow rate per unit volume in the contact section, that is, the space velocity (SV). Referring to the heating temperature in the contact section, if the temperature difference relative to the boiling point of the material to be distilled is insufficient, entrained droplets in the contact section may not be completely revaporized at the surface of the contact members. Whereas if the temperature difference is greater than 200° C., there is a problem that the vapor pressures of the impurities increase. Also, that will be uneconomical as more energy will be required. Then, referring to the velocity of the vapors of the materials being distilled passing through the inside of the contact section, it requires a long period of time for the purification if the velocity is too slow. Heat exchange efficiency in the contact section is reduced and entrainment cannot be prevented if the velocity is excessively fast.

As the material which is to be purified by the method and apparatus according to this invention, any material may be used so long as it can be purified by distillation and preferred are those where entrainment is a problem. Particularly suitable specific examples of the material to be purified can include, for example, inorganic acids such as hydrochloric acid, nitric acid, hydrofluoric acid, perchloric acid, hydroiodic acid, organic acids such as acetic acid and formic acid, organic solvents, such as acetone, chloroform, trichloroethylene and carbon tetrachloride, as well as water. Further, the impurities separated and eliminated by the method and apparatus according to this invention are non-volatile impurities introduced in trace amounts during manufacture of the material to be distilled, and can include, for example, metal impurities such as aluminum Al), iron (Fe), calcium (Ca), copper (Cu), magnesium (Mg), manganese (Mn), sodium (Na) and potassium (K) or various high molecular impurities of unknown structures.

In the case of producing chemicals of high purity by the method and apparatus according to this invention, if super high purification up to impurity levels of parts per million or parts per trillion is required, the apparatus is, desirably, installed entirely in a clean room and the receiver for liquid condensates is operated on a clean bench.

Further, the production method and apparatus according to this invention may be batchwise or of the continuous type, depending on the kind, the amount, and the required purity of the material to be distilled.

In this invention, since the contact section is heated to a temperature higher than the boiling point of the material being distilled, the droplets of the material being distilled entraining non-volatile impurities are completely vaporized leaving the non-volatile impurities in the contact section. Thus, the non-volatile impurities carried by entrainment to the contract section are collected in the contact section and, as a result, the purity of the distilled liquid condensed in the condensing section is improved.

In the production method and apparatus according to this invention, it is possible to produce chemicals of high purity low in nonvolatile impurities, particularly metal impurities or high molecular weight impurities, easily and at a reduced cost.

DETAILED DESCRIPTION OF PREFERRED EMBODIMENTS Example 1

Figure 1:
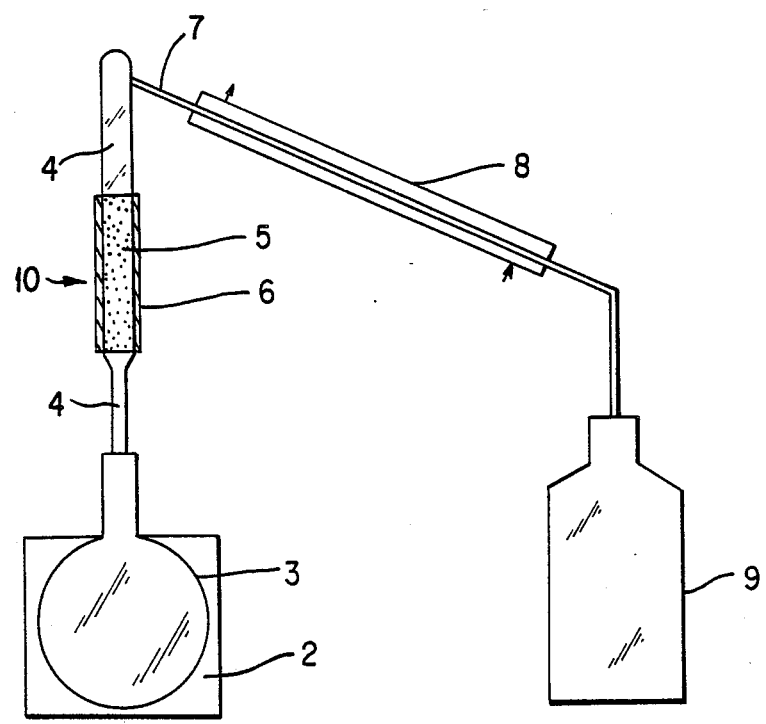
FIG. 1 is a schematic view illustrating the apparatus of the present invention.
Figure 2:
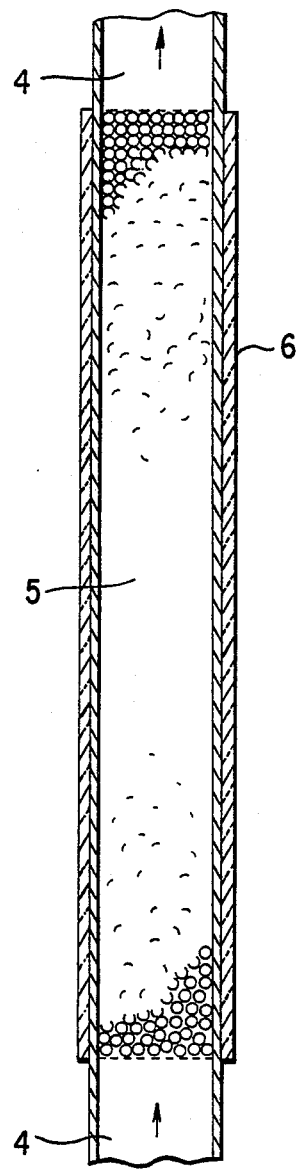
FIG. 2 is a cross sectional view of a contact section of a distillation apparatus used for the purification of hydrochloric acid according to an embodiment of the invention.

As shown in FIGS. 1 and 2, a quartz column 4, 350 mm in length×22.2 mm in diameter, was connected to a 2 liter volume round bottom flask 3 made of Pyrex, and 12 g of pulverized silica gel, 2 mm grain size, was packed as the contact member 5 in a 200 mm length in the quartz column to constitute a contact section 10. Further, a band heater 6, as heating means, was wound around the outer side of the contact section 10, a teflon tube 7 having a cooler or condenser 8 was connected to the top of the quartz column 4, a 2 liter volume receiver 9 made of teflon was connected to the lower end of the teflon tube. The receiver was installed on a Class 100 clean bench and, further, the entire apparatus thus assembled was installed in a clean room.

Hydrochloric acid of high purity was prepared by charging 1.5 liter of 20.22 wt % hydrochloric acid containing Al, Cu, Mg, Mn, Na and K, 50 ppm each (50,000 ppb) as the metal impurities into the round bottom flask 3, heating the contact section 10 by the band heater 6° to 150°±5° C. higher by about 31° C. than the 108.58° C. boiling point of hydrochloric acid, heating the round bottom flask being immersed in a hot medium bath 2, as the heating section, and setting the space velocity in the contact section 10 to 0.75 sec$^{-1}$ and the distillation rate to 100 ml/hr.

In this case, 100 ml of the distillate was removed, and then 700 ml of distillate was collected in the receiver 9 and the amounts of the metal impurities Al, Fe, Ca, Cu, Mg, Mn, Ma and K for the thus obtained hydrochloric acid were measured using a flameless electron absorption device. The results are shown in Table 1.

Comparative Example 1

20.22 wt % hydrochloric acid was purified using the same procedures as in Example 1 above except that the contact section 10 was not heated. The amounts of the metal impurities Al, Fe, Ca, Cu, Mg, Mn, Na and K for the thus obtain hydrochloric acid were also measured using a flameless electron absorption device. The results are shown in Table 1.

TABLE 1

| Impurity metal | Impurity content (ppb) | |
|---|---|---|
| | Example 1 | Comparative Example 1 |
| Al | <0.050 | 2.50 |
| Fe | 0.057 | 3.10 |
| Ca | <0.020 | 2.80 |
| Cu | 0.020 | 3.00 |
| Mg | <0.005 | 3.50 |
| Mn | <0.005 | 2.40 |
| Na | <0.005 | 2.80 |
| K | <0.005 | 2.50 |

EXAMPLE 2

Figure 3:
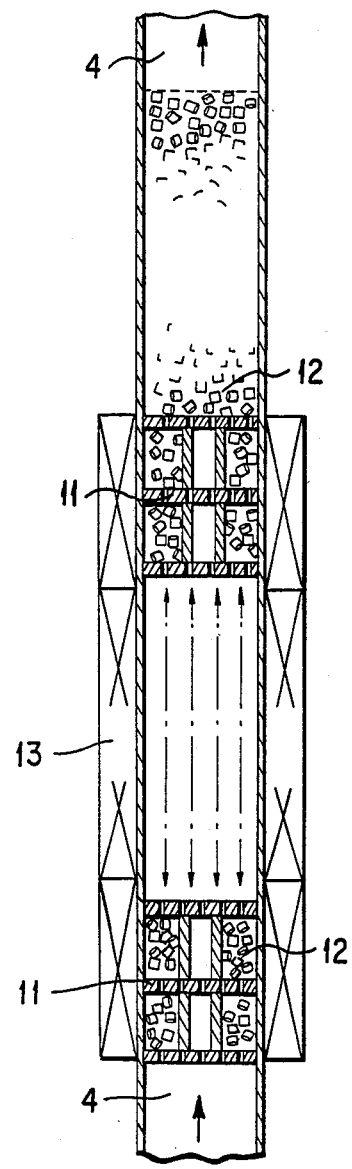
FIG. 3 is a cross sectional view of a contact section of a distillation apparatus used for the purification of hydrofluoric acid according to another embodiment of the invention.

As illustrated in FIGS. 1 and 3, column 4 made of teflon and 500 mm in length and 40 mm in diameter was connected to a 2 liter volume flask 3 also made of teflon. Perforated carbon plates, 12 mm×38 mm $\phi$, and teflon tubes 11, 20 mm×20 mm $\phi$, were alternatively stacked, 12 stages in total, over the 300 mm length of the teflon column. Raschig rings 12 made of teflon, 5 mm outer diameter×3 mm inner diameter×5 mm length, were packed in the stacked portion and for 150 mm height over the stacked portion to constitute a contact section 10. A heating section 13 of a high frequency induction heating device (electronic range) was attached, as the heating means, to the outside of the contact section 10. A teflon tube 7 equipped with a cooler or condenser 8 was connected to the top of the teflon column 4, a 2 liter volume receiver 9 made of teflon was connected to the lower end of the teflon tube. The receiver was set on a class 100 type clean bench and, further, the thus assembled entire apparatus was installed within the clean room.

Then, hydrochloric acid of high purity was prepared using the same procedures as described in Example 1 by charging 15 liter of 38.2 wt % hydrofluoric acid containing Al, Cu, Mg, Mn, Na and K 50 ppm each (50,000 ppb) as the metal impurities in the still, heating the contact section 10 by the high frequency induction heating device 13 to 160°±5° C. higher by about 47.8° C. than the 112.2° C. boiling point of the hydrofluoric acid, heating the still by immersing it in a hot medium bath 2, and setting the space velocity of 0.1 sec$^{-1}$ and distillation rate at 100 ml/hr in the contact section 10.

In this case, as in Example 1, 100 ml of the distillate forerun was removed, and then 700 ml of distillate was collected in the receiver and the amounts of the metal impurities Al, Fe, Ca, Cu, Mg, Mn, Na and K in the hydrofluoric acid thus obtained were measured in a flameless electron absorption device. The results are shown in Table 2.

Comparative Example 2

38.2 wt % hydrochloric acid was purified using the same procedures as in Example 2 except that the contact section 10 was not heated. The amounts of the metal impurities Al, Fe, Ca, Cu, Mg, Mn, Na and K in the thus obtained hydrochloric acid were measured using a flameless electron absorption device. The results are shown in Table 2.

TABLE 2

| Impurity metal | Impurity content (ppb) | |
|---|---|---|
| | Example 2 | Comparative Example 2 |
| Al | <0.050 | 3.75 |
| Fe | 0.035 | 4.65 |
| Ca | <0.020 | 4.20 |
| Cu | 0.015 | 4.50 |
| Mg | <0.005 | 5.25 |
| Mn | <0.005 | 3.60 |
| Na | <0.005 | 4.20 |
| K | <0.005 | 3.75 |

What is claimed is:

1. A method for the distillation in a distillation device of an inorganic acid having non-volatile matter impurities therein, said distillation device comprising a heating section, a contacting section and a condensing section, to obtain the inorganic acid essentially free of non-volatile matter impurities, said method consisting essentially of:
   (a) boiling the inorganic acid in the heating section to form vapors of the inorganic acid;
   (b) contacting the vapors of the inorganic acid from the heating section with a contact member inert to said vapors in the contacting section, said vapors being passed through the contacting section at a flow rate of 0.01 to 10 sec$^{-1}$ per unit volume of the contacting section;
   (c) heating the contacting section at a temperature of 1 to 100° C. higher than the boiling point of the inorganic acid being distilled and maintaining the inorganic acid completely vaporized in the contacting section; and
   (d) condensing the vapors from the contacting section in the condensing section.

2. A method according to claim 1, wherein the inorganic acid is hydrochloric acid, nitric acid, hydrofluoric acid perchloric acid or hydroiodic acid.

3. A method according to claim 1, wherein the impurities are metal impurities.

4. A method according to claim 1, wherein the contact member is silica gel, alumina, teflon, glass, quartz or graphite.

* * * * *

UNITED STATES PATENT AND TRADEMARK OFFICE
CERTIFICATE OF CORRECTION

PATENT NO. : 4,892,625
DATED : January 9, 1990
INVENTOR(S) : SHIMIZU et al

It is certified that error appears in the above-identified patent and that said Letters Patent is hereby corrected as shown below:

On the cover page, Item [73], "Tama Chemicals Co., Ltd., Japan; Moses Lake Industries, Inc., Japan" should read --Tama Chemicals Co., Ltd., Tokyo, Japan; Moses Lake Industries, Inc., Moses Lake, WA.--.

Signed and Sealed this

Second Day of April, 1991

Attest:

HARRY F. MANBECK, JR.

*Attesting Officer*      *Commissioner of Patents and Trademarks*